United States Patent [19]
Baumgardner

[11] Patent Number: 5,820,626
[45] Date of Patent: Oct. 13, 1998

[54] COOLING LASER HANDPIECE WITH REFILLABLE COOLANT RESERVOIR

[75] Inventor: Jonathan M. Baumgardner, Auburn, Calif.

[73] Assignee: Laser Aesthetics, Inc., Auburn, Calif.

[21] Appl. No.: 692,929

[22] Filed: Jul. 30, 1996

[51] Int. Cl.$^6$ .......................... A61B 17/36; A61B 17/38
[52] U.S. Cl. ................. 606/13; 606/15; 606/20
[58] Field of Search .................. 606/9, 10, 11, 606/12, 14, 15, 16, 17

[56] References Cited

U.S. PATENT DOCUMENTS

| | | | |
|---|---|---|---|
| 3,630,203 | 12/1971 | Sellinger et al. | |
| 3,821,510 | 6/1974 | Muncheryan | 606/16 X |
| 4,376,376 | 3/1983 | Gregory | 62/51 |
| 4,860,744 | 8/1989 | Johnson et al. | 606/20 |
| 5,020,995 | 6/1991 | Levy | 433/215 |
| 5,057,104 | 10/1991 | Chess | 606/9 |
| 5,098,428 | 3/1992 | Sandlin et al. | 606/22 |
| 5,196,004 | 3/1993 | Sinofsky | 606/3 |
| 5,275,595 | 1/1994 | Dobak, III | 606/20 |
| 5,344,418 | 9/1994 | Ghaffari | 606/9 |
| 5,468,238 | 11/1995 | Mersch | 606/15 |
| 5,520,682 | 5/1996 | Baust et al. | 606/20 |

OTHER PUBLICATIONS

Selective cooling of biological tissues: application for thermally mediated therapeutic procedures, Anvari et al., Phys. Med. Biol. 40 (1995) 241–252.

Handpiece Extender brochure, Spectrum Medical Technologies, Inc., RD–1100, RD–1200, 2 pages.

*Primary Examiner*—Jennifer Bahr
*Assistant Examiner*—Sonya Harris-Ogugua
*Attorney, Agent, or Firm*—Ray K. Shahani

[57] ABSTRACT

A laser handpiece apparatus for use in therapeutic procedures employing selective cooling, the apparatus for use in conjunction with a controllable laser source, the apparatus including laser delivery device for controllably delivering a predetermined amount of laser energy to a preselected surface area, a reservoir having a predetermined volume, cryogen liquid contained in the reservoir, and a valve for controllably delivering a portion of the cryogen liquid to the preselected surface area.

16 Claims, 3 Drawing Sheets

COOLING LASER HANDPIECE WITH REFILLABLE COOLANT RESERVOIR

FIELD OF THE INVENTION

This invention relates to laser delivery devices for use in medical and other applications, and more particularly, to a hand-held laser delivery apparatus with a refillable coolant liquid reservoir for use in methods and techniques utilizing dynamic cooling.

BACKGROUND OF THE INVENTION

In medical and other types of laser applications, laser delivery handpieces are widely used. With the development of optical fibers and solid-state lasers, complex arrangements of collimating lenses, mirrors and filters have been replaced with small, efficient laser delivery devices utilizing fiber optics.

U.S. Pat. No. 5,020,995 issued Jun. 4, 1991 to Levy teaches a surgical treatment and method for cutting tooth tissue. A handpiece for cutting dentin and enamel is disclosed which contains a hollow tube connected to an external source of cooling liquid. The apparatus has a number of drawbacks, however, including the need for peripheral tubing and other connections to control and laser source. In practice, these plurality of external connections make the device awkward to use. Furthermore, if the coolant source is located farther than about 0.5 to about 1.0 meter from the outlet end positioned to direct coolant onto the tissue being cooled, either significant insulation is required or a considerable purge time will be necessary to deliver coolant liquid at a low temperature to the desired location on demand.

U.S. Pat. No. 5,344,418 issued Sep. 6, 1994 to Ghaffari teaches an optical system for treatment of vascular lesions. In addition to the drawbacks noted above, principally the need for external connections and complicated piping, insulation and purging requirements, the cooling system in intended to cool the sapphire lens of the system. The patent also refers to a system for the control of skin temperature.

Recently, a great deal of attention has been given to selective cooling of biological tissue during thermally mediated therapeutic procedures. B. Anvari et al., *Selective Cooling of Biological Tissues; Application for Thermally Mediated Therapeutic Procedures*, Phys. Med. Biol. 40 (1995) 241–252. Methods and systems have been proposed based on models of heat conduction in various types of tissue at various levels beneath the skin. In certain dermatological applications the objective has been to produce irreversible thermal damage to subsurface tissue constitutes without destroying or altering superficial structures. Examples of such procedures include laser treatment of port wine stains and the clinical treatment of other dermatoses, lesions and tattoos. Experiments have been performed that use, for example, infrared radiometry to measure the thermal response of in vivo human skin to cooling by a cryogen spurt.

While a information has been gained from these studies and others about the effect of such cooling on biological tissue during such operations, very little effective or efficient equipment is commercially available. Often, applying spurts of cryogenic materials to the site of laser delivery results in splashing and unconfined cooling.

Therefore, it an advantage of the present invention to provide an improved handpiece for performing thermally mediated therapeutic and cosmetic procedures with selective cooling of biological tissue.

It is a further advantage of the present invention to provide a light, unrestricted handpiece for such procedures.

It is a further advantage of the present invention to provide an apparatus with an on-board cryogenic material or other coolant liquid reservoir.

It is a further advantage of the present invention to provide such apparatus which allows visualization of the remaining amount of coolant liquid and which is refillable.

It is a further advantage of the present invention to provide such apparatus in which both coolant and laser energy are both delivered in a controlled, confined manner to avoid delivery of both laser energy and coolant to undesired locations.

SUMMARY OF THE INVENTION

The invention disclosed herein is a laser handpiece apparatus for use in therapeutic procedures employing selective cooling. The apparatus is intended for use in conjunction with a controllable laser source. The apparatus comprises a laser delivery means for controllably delivering a predetermined amount of laser energy to a preselected surface area, reservoir means having a predetermined volume, cryogen liquid contained in the reservoir means, and valve means for controllably delivering a portion of the cryogen liquid to the preselected surface area. A preferred embodiment comprises delivery tube means having a proximal and a distal end, the laser delivery means and the valve means coupled to the delivery tube such that both the laser energy and the portion of the predetermined volume of cryogen are controllably delivered to the preselected surface area. In a preferred embodiment, the reservoir comprises a transparent tube, thus providing a visual indication of the volume or cryogen liquid remaining in the reservoir. In a preferred embodiment, the valve means comprises a controllable solenoid valve. A preferred embodiment, comprises a laser delivery means focusing means.

Numerous other advantages and features of the present invention will become readily apparent from the following detailed description of the invention and the embodiments thereof, from the claims and from the accompanying drawings in which the details of the invention are fully and completely disclosed as a part of this specification.

DETAILED DESCRIPTION OF THE INVENTION

The feasibility of selectively cooling biological tissues has been explored experimentally. Infrared radiometry can be used to measure the thermal response of in vivo human skin to cooling by a cryogen spurt. One model assumes a two-layered semi-infinite medium consisting of skin in contact with a cold film whose thickness may change with time. The term "boundary layer" refers to a film of cryogenic material in contact with both air and skin. When cryogen is spurted onto the skin surface, skin temperature is reduced as a result of supplying the latent heat of vaporization. As the skin surface temperature approaches the boiling point of the cryogen, the rate at which cryogen droplets evaporate becomes less than the accumulation rate or cryogen on the surface.

Figure 1:
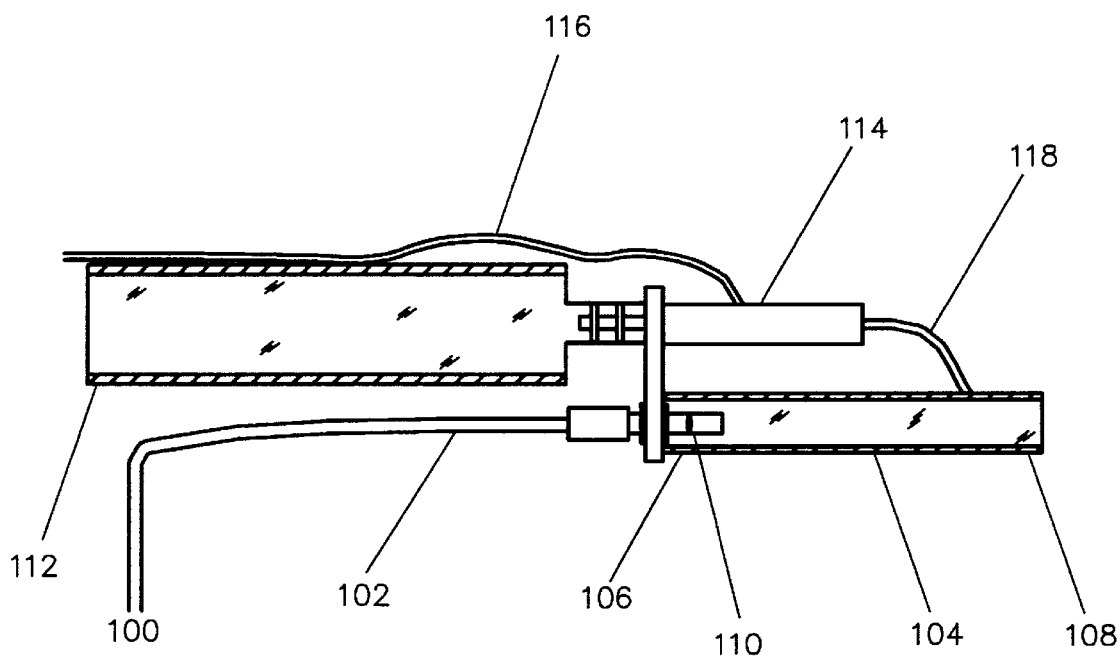
FIG. 1 is a representative view of the laser handpiece with refillable coolant reservoir for dynamic, selective cooling of biological tissue during thermally mediated therapeutic and cosmetic procedures.

FIG. 1 is a representative view of the laser handpiece with refillable coolant reservoir for dynamic, selective cooling of biological tissue during thermally mediated therapeutic and cosmetic procedures. A laser source 100 is connected to laser delivery means 102. Laser delivery means typically contain a fiber optic cable, a fiber bundle or other fiber optic device. While the present invention may be fully operable and efficacious utilizing a CO2 laser, it will be understood that the present invention is especially suited for use with those laser sources capable of being transmitted conveniently via optical fibers. These laser sources include Q-switched ruby lasers, flashlamp-pumped type pulsed dye lasers, Nd:YAG, Holmium-type and other solid-state lasers in use and known currently or in the future.

A transparent delivery tube 104 is positioned at the distal end of the laser delivery means. Laser energy enters the delivery tube at proximal end 106 and radiates from the tube at distal end 108. In a preferred embodiment of the apparatus, the laser delivery means includes a focusing means 110 adjacent the proximal end of the delivery tube. It will be understood that in other preferred embodiments the focusing means is located adjacent the distal end of the delivery tube or elsewhere within the apparatus, and in other preferred embodiments a plurality of focusing means are located at different positions within the apparatus. It will be understood that a great variety of design factors must be considered and will be included in the scope of the present invention. There are several benefits to providing focusing means integral with or separate from the laser delivery means, including creation of different spot sizes, optimization depending upon the application, e.g. blanching of port wine stains, photoablation in a cutting or tissue removal application, etc. The length of the delivery tube may vary depending upon the desired spot size, the need to provide an extending tip and the type of laser delivery means used. The focusing means is also adjustable in preferred embodiments. Typical laser delivery device delivery tubes such as those known as Handpiece Extenders, Part Nos. RD-1100 and RD-1200 made by Spectrum Medical Technologies, Inc. in Natick Mass. are commercially available.

The delivery tube is preferably transparent and tubular, but can have a plurality of different cross sectional geometries. The design of the delivery tube will prevent possible "fly-away" of ablated tissue, cells or blood, providing protection from cross contamination for other inhabitants and equipment in the operating room. The tube will also direct the liquid cryogenic material to specific areas conveniently. Waste of cryogen and loss of containment thereof as well as the risk for unintended contact with the cryogenic material is also minimized thereby. The transparent tube also provides the physician or technician with an unobstructed view of the treatment in progress. Preferred embodiments have enhanced transmitting features, including anti-reflection coatings to protect the internal optical system and eliminate the potential for energy backlash, and perpendicular positioning means which reduce the risk of reflected light which could otherwise create a vision hazard in the operating room.

Cryogenic material is delivered to the distal end of the delivery tube, or to another position thereon, from a reservoir 112 through controllable valve means 114. Freon and liquid CO2 have been widely used cryogenic materials and are well known in the field of cryosurgery. An appropriate cryogen spray would be 1, 1, 1, 2- tetrafluoroethane, $C_2H_2F_4$, an environmentally compatible, non-toxic, non-flammable freon substitute. Other cryogenic materials, such as 134R (also a freon substitute), may also be used and will be apparent to those skilled in the art.

In a preferred embodiment, the reservoir consists of a tube between about 0.25 and 1.0 inches in diameter of an appropriate length, manufactured out of plastic, glass or other suitable material. The reservoir will have a volume of between about 100 and 500 milliliters, or more or less as may be desired or necessary for particular applications.

In preferred embodiments, the reservoir can be either refillable or replaceable. In the refillable embodiment, suitable nozzle cap or other fill means is provided on the reservoir. In the replaceable embodiment, the reservoir is a disposable canister which can be purchased in advance and stocked at the hospital or clinic. A suitable attachment or mounting means is provided to conveniently, efficiently and safely remove an empty reservoir when empty and replace it with a full canister. The reservoirs have either threaded end fittings or bayonet-type locking means for providing a leak-proof, secure attachment between the reservoir and rest of the handpiece. It will be apparent to those skilled in the art that the disposable and replaceable coolant reservoirs can be manufactured with a wide range of variation in attachment means, volume, shape and materials, all of which are included in the scope of this invention.

Flow from the reservoir through the valve means is controlled manually or otherwise. The valve means can be a low-temperature solenoid-type valve which delivers spurts of cryogen in bursts. Common automotive or other industrial liquid fuel injectors can also be used. Delivery of spurts between about 10 milliseconds and about 500 milliseconds in length are possible with various types of valves. Typically, the solenoid valve is able to withstand pressures of up to about 80 to 100 PSI and temperatures as low as about −30 to −40 degrees Celsius.

After passing through the valve means, the cryogenic material is directed into the delivery tube adjacent the distal end, or the proximal end, of the delivery tube. Controller wires 116 will actuate the valve means, as desired, allowing cryogen to flow into the delivery tube via cryogen transport tube 118. In a preferred embodiment, the valve means delivers cryogen directly into the delivery tube means, and in another preferred embodiment, a spraying nozzle means is employed such that the cryogen is sprayed onto a preselected surface area in a predetermined pattern or at a predetermined flowrate, velocity, etc.

As described above, various dynamic cooling protocols, methods and systems are well known for use with thermally mediated treatment of biological tissue and other materials. Simultaneously or alternatingly, predetermined amounts of laser energy as well as cryogenic coolant can be delivered to the operating site precisely according to temperature and position sensors and on-board computing means associated with the laser source. Controllers based upon theoretically-derived or actually measured operating parameter data will allow the physician or technician to maintain a predetermined thermal gradient or temperature profile throughout certain preselected tissue. These control schemes will be possible with the apparatus of the present invention and particular or individual control schemes for specific applications will be apparent to those skilled in the art. A preferred embodiment of the present invention includes a timing circuit to control according to predetermined operating parameters time and rate of laser energy delivery, time and rate of cryogen delivery, sequencing and overlap of those events with ablation, cooling periods, etc.

A preferred embodiment of the present invention comprises a temperature sensor means located at the distal end of the delivery tube. The temperature sensor will sense the temperature of either the tip of the delivery tube, the skin upon which the laser energy and the coolant are directed, or both. Temperature probes and methods are well known in the art. Such temperature sensors operate in a variety of different ways, including black-body type radiation sensors, thermocouples, thermometers, etc. The temperature sensor provides information to a controller with feedback control of the laser, coolant delivery switch, etc.

A preferred embodiment of the present invention comprises a laser and/or cryogen interlock system. In the event the handpiece is held such that vapors in the reservoir are delivered before liquid, a substantial decrease in cooling effect is observable. Venting of cryogen fumes is very inefficient relative to the degree of cooling which can be achieved using liquid cryogen. Unless the surgeon is careful, during operation the handpiece can be manipulated in such a way as to tilt or turn the handpiece so that the liquid cryogen flows away from the solenoid or other flow valve. To prevent discharge of vapors, and sometimes more importantly, to prevent delivery of laser energy in the absence of sufficient coolant an interlock system is used. This system can be configured in a number of different ways, as will be apparent to those skilled in the art. Mercury switches to prevent switch actuation at certain orientations are widely used. Integrated circuits and other types of microprocessors or micro-devices are also available for such level control. Such a device ensures adequate orientation, such as a vertical position, of the handpiece prior to delivery of laser energy. Additionally, the interlock can be tied into a temperature sensor/control circuit. Such a circuit ensures a suitably low temperature at the skin surface or at a distal point on the valve or delivery tube prior to permitting delivery of laser energy. Another embodiment of the preferred embodiment measures liquid flow through the valve. Such apparatus prevents delivery of laser energy until and unless liquid cryogen is flowing at a predetermined minimum rate.

Figure 2:
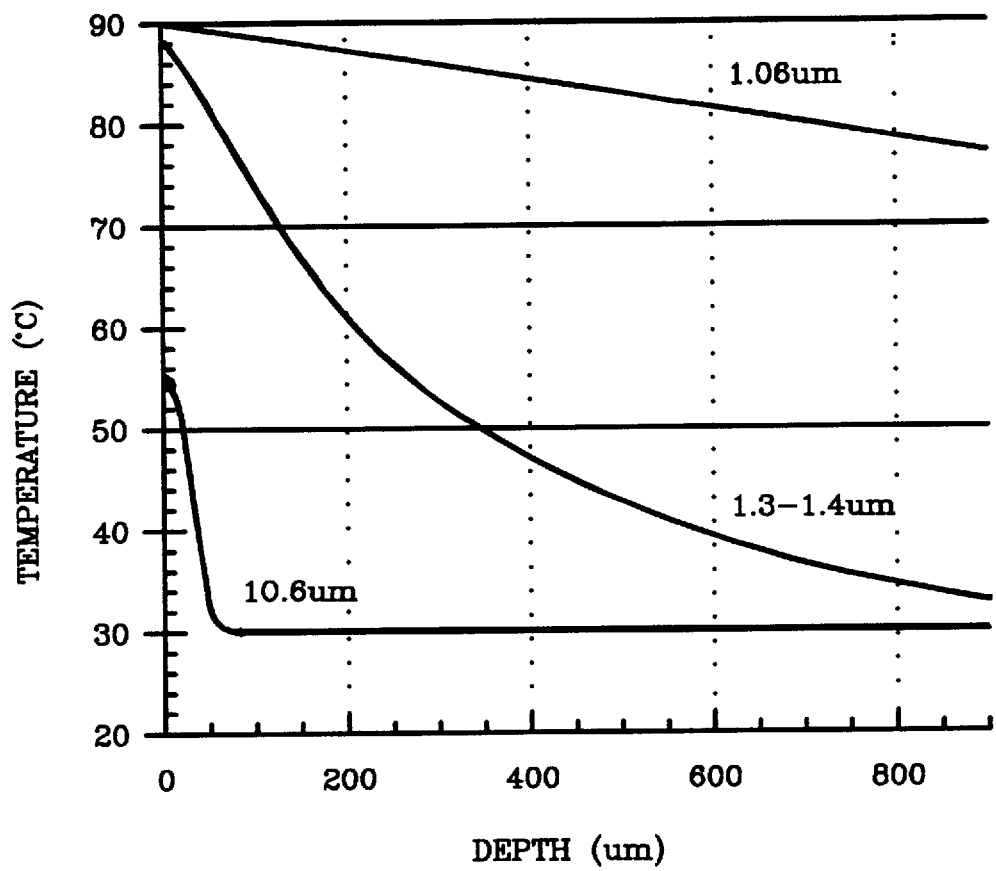
FIG. 2 is a graph demonstrating the temperature gradient through a portion of the skin without precooling as a function of both the wavelength of incident laser energy and the depth of laser radiation penetration.

FIG. 2 is a graph demonstrating the experimentally obtained temperature gradient through a portion of the skin without precooling as a function of both the wavelength of incident laser energy and the depth of laser radiation penetration. The graph demonstrates a change in temperature ($\Delta T$) of about 60 degrees Celsius and all curves are shown for the time point 1 millisecond following exposure to the laser energy. The graph shows three lines corresponding to laser wavelengths of 10.6 microns, 1.3–1.4 microns and 1.06 microns.

Figure 3:
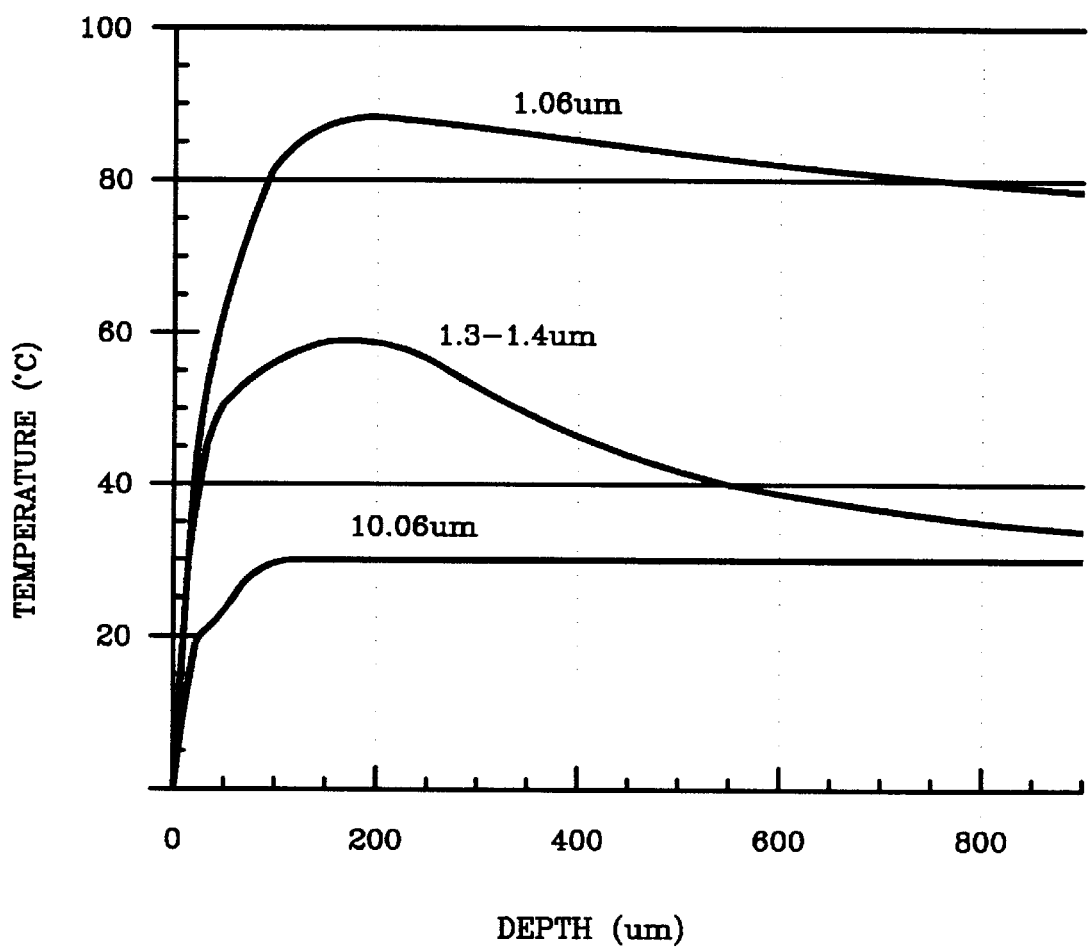
FIG. 3 is a graph demonstrating the temperature gradient through a portion of the skin with precooling as a function of both the wavelength of incident laser energy and the depth of laser radiation penetration.

FIG. 3 is a graph demonstrating the temperature gradient through a portion of the skin with precooling as a function of both the wavelength of incident laser energy and the depth of laser radiation penetration. The graph demonstrates a change in temperature ($\Delta T$) of about 60 degrees Celsius. In these experiments, precooling of the skin surface tissue for a period of 20 milliseconds was conducted immediately prior to exposure to laser energy. All curves are shown for a time point 1 millisecond following exposure to the laser energy. The graph shows three lines corresponding to laser wavelengths of 10.6 microns, 1.3–1.4 microns and 1.06 microns. It will be understood that the parameters of time, cooling and exposure to laser energy may be varied manually or automatically, as desired.

Studies have shown that irradiating tissue with a midinfrared laser source through a surface thermal absorption element or heat sink permits an optimum thermal profile within the target tissue with near physiologic temperature at the surface of the irradiated surface thus minimizing surface thermal damage. In the case of desired thermal collagen shrinkage, this is clearly the desired condition. Others have shown that attenuating the surface temperature before laser irradiation and therefore creating a boundary layer on the skin surface can result in selective cooling of the target tissue thus preserving the normal overlying epidermis.

During a typical dynamic cooling process, the surface of the skin is pre-cooled to as low as 0 degrees Celsius or lower, at a rate fast enough to cool the surface only but not dissipate heat from below about 400–500 microns below the surface. In a preferred embodiment, during the cooling step the target tissue remains at body temperature and is not cooled at all.

For example, in laser-induced shrinkage of collagen tissue, by applying cooling to the surface of the skin for a short period of time, typically between about 5 and 100 milliseconds, and then delivering laser energy, the surface is initially cooled but the target tissue never is. Generally, the surface layer of skin is rapidly cooled. A high rate of cooling will prevent proximal hypothermia and will also tend to have a numbing, anesthetic or analgesic effect. Therefore, upon delivery of laser energy onto the surface and therethrough, the target tissue will be raised to the optimal thermal shrinkage temperature and generally not any higher, in an adequately rapid process.

In a preferred embodiment of the method of the present invention, cooling and heating are performed in a predetermined timing sequence, optionally with the use of timer circuits and/or other controller means.

With respect to studies performed removing sub-dermal skin lesions, such as port wine stains and other red or brown marks, an optimum cooling strategy might be one that uses a short spurt of cryogen (e.g., 5–20 ms) to reduce the local temperature in the pigmented epidermis, while minimizing attenuation of the laser light by the boundary layer, followed by post-irradiation cooling spurt that provides a heat sink for dissipation of the epidermal heat generated by melanin absorption.

While the principles of this invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The scope of the present invention is intended to cover any application or procedure, including therapeutic, medical, industrial and other, in which selective cooling is desirable in conjunction with the delivery of laser energy. The appended claims are intended to cover and embrace any and all such modifications, within the limits only of the true spirit and scope of the inventention.

We claim:

1. A laser handpiece apparatus for use in therapeutic and other procedures employing selective cooling, the apparatus for use in conjunction with a controllable laser source, the apparatus comprising:

laser delivery means for controllably delivering a predetermined amount of laser energy to a preselected surface area;

removable reservoir means integral with the laser delivery means having contained therein a predetermined volume of cryogenic liquid;

valve means for controllably delivering a portion of the cryogen liquid to the preselected surface area; and releasable attachment means for securely and releasably coupling the reservoir directly to the valve means.

2. The apparatus of claim 1 further comprising delivery tube means having a proximal and a distal end, the laser delivery means and the valve means coupled to the delivery tube such that both the laser energy and the portion of the predetermined volume of cryogen are controllably delivered to the preselected surface area.

3. The apparatus of claim 1 in which the reservoir comprises a transparent tube, thus providing a visual indication of the volume of cryogen liquid remaining in the reservoir.

4. The apparatus of claim 1 in which the valve means comprises a controllable solenoid valve.

5. The apparatus of claim 1 further comprising means for focusing the laser energy.

6. The apparatus of claim 1 in which the reservoir is refillable, the apparatus further comprising a refill valve means.

7. The apparatus of claim 1 in which the attachment means comprises matching threaded end fittings on both the reservoir and the valve means.

8. The apparatus of claim 1 in which the attachment means comprises a locking bayonet-type mounting.

9. The apparatus of claim 1 further comprising temperature sensor and feedback control means for preventing undesirable delivery of laser energy.

10. The apparatus of claim 1 further comprising a laser delivery interlock means for preventing undesirable delivery of laser energy.

11. The apparatus of claim 10 in which the laser delivery interlock means includes a level switch.

12. The apparatus of claim 10 in which the laser delivery interlock means includes a temperature sensor.

13. The apparatus of claim 10 in which the laser delivery interlock means includes a liquid flow sensor.

14. A method of performing a therapeutic procedure involving delivery of laser energy to preselected surface areas, the method comprising the following steps:

(a) providing a laser handpiece apparatus, the apparatus comprising laser delivery means, removable reservoir means integral with the laser delivery means having a predetermined volume of cryogenic liquid contained therein, valve means for controllably delivering a portion of the cryogen liquid, and releasable attachment means for securely and releasably coupling the reservoir directly to the valve means;

(b) controllably delivering a predetermined amount of cryogen liquid to the preselected surface areas;

(c) controllably delivering a predetermined amount of laser energy to the preselected surface areas;

(d) interrupting delivery of laser energy when the cryogen liquid reservoir means is empty;

(e) releasing attachment means and removing entry cryogen liquid reservoir means; and (f) replacing the empty cryogen liquid reservoir means with a full one for continued delivery of both cryogen liquid and laser energy from the handpiece, as desired.

15. The method of claim 14 wherein step (f) is replaced with the following step:

(g) refilling the reservoir with cryogen liquid coolant.

16. The method of claim 14 further comprising the following step:

(h) visually monitoring the volume of cryogen liquid retained in the reservoir means.

* * * * *